United States Patent [19]

Braxton

[11] 4,285,077

[45] Aug. 25, 1981

[54] APPARATUS FOR EXTRACTING PROTEINS FROM URINE

[76] Inventor: Earl J. Braxton, 46731 Shelby Rd., Utica, Mich. 48087

[21] Appl. No.: 76,894

[22] Filed: Sep. 19, 1979

Related U.S. Application Data

[63] Continuation-in-part of Ser. No. 901,248, Apr. 28, 1978, abandoned.

[51] Int. Cl.³ ............................................. A47K 4/00
[52] U.S. Cl. .......................................... 4/462; 4/449; 4/144.1; 4/459
[58] Field of Search ................... 4/459, 449, 462, 301; 435/215, 216, 815

[56] References Cited

U.S. PATENT DOCUMENTS

| | | | |
|---|---|---|---|
| 3,477,912 | 11/1969 | Sloane | 435/215 |
| 3,602,923 | 9/1971 | Girala | 4/144.1 |
| 3,711,377 | 1/1973 | Sloane | 435/215 |
| 3,745,592 | 7/1973 | Novak | 4/301 |
| 3,755,083 | 8/1973 | Novak | 435/215 |
| 3,835,480 | 9/1974 | Harding | 4/459 |
| 4,025,390 | 5/1977 | Urakawa et al. | 435/215 |
| 4,048,014 | 9/1977 | Urakawa et al. | 435/215 |

*Primary Examiner*—Henry K. Artis
*Attorney, Agent, or Firm*—Krass, Young & Schivley

[57] ABSTRACT

Pharmaceutically useful trace elements contained in human urine are collected by disposing a filter body containing an adsorbent for the trace elements in the gravity flow line connecting the unflushed urinal of a portable toilet to its holding tank. The portable toilet also includes a seat connected to the holding tank by a separate gravity feed line. The holding tank contains an odor reducing chemical solution for the urine and fesces. A filter body supported in the conduit between the urinal and the holding tank consists of an adsorbent for the trace constituents of the urine that it is desired to extract. Urine voided into the urinal passes through the adsorbent filter body before going to the holding tank. When the holding tank of the portable toilet is pumped clean and the deoderizing solution replaced, the filter body is removed and processed to extract the trace constituents replaced with an unsaturated filter body.

8 Claims, 3 Drawing Figures

U.S. Patent     Aug. 25, 1981     4,285,077
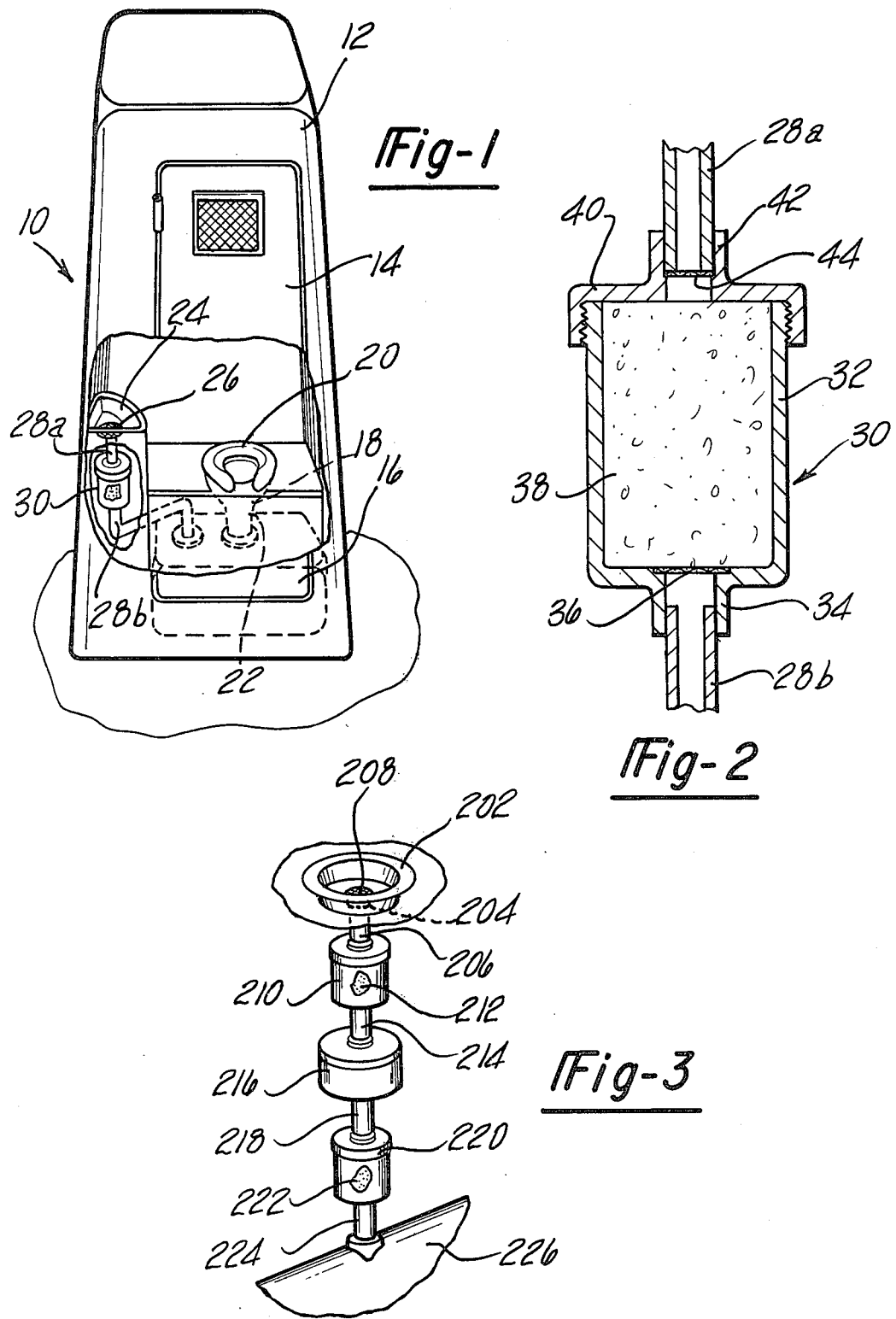

APPARATUS FOR EXTRACTING PROTEINS FROM URINE

REFERENCE TO RELATED APPLICATIONS

This application is a continuation-in-part of application Ser. No. 901,248, filed Apr. 28, 1978 entitled "Urine Extraction System", now abandoned.

BACKGROUND OF THE INVENTION

1. Field of the Invention

This invention relates to a method and apparatus for extracting useful biological trace constituents from urine through use of adsorbent filters placed in the gravity flow line between a flushless urinal and the holding tank of a portable toilet.

2. Prior Art

Human urine contains small percentages of a variety of proteins and especially enzymes which have commercial value, usually as pharmaceuticals. For example, the enzyme Urokinase, which is present in trace percentages in human urine, is widely used as an anti-clotting agent for blood and in connection with treatment for cancer because of its ability to dissolve the fibrin growths which sometimes sheath carcinogenic cells. Most of the commercial supply of Urokinase is now derived from urine by the collection of urine from paid donors who regularly visit central collection stations. Within a few hours of being collected the urine is transported to a central processing station where it is intermixed with adsorbents that attract the large protein molecules of interest. The collected proteins are then eluted off the adsorbents and the extract is processed and purified to derive the Urokinase or other commercially useful proteins. U.S. Pat. No. 3,755,083 discloses a process of this type.

Urokinase enzymes rapidly degenerate at normal collection temperatures so that it is necessary to process the urine as soon as possible after it is collected. The resulting collection and processing costs and the low percentage of Urokinase contained in urine result in a very high unit cost, severely limiting pharmaceutical use of the material.

As a more economical alternative to this process of collecting quantites of urine and then delivering them to a processing station, U.S. Pat. No. 3,711,377 to Sloane discloses a Urokinase collection process employing a tray filled with an adsorbent and adapted to be supported within the urinal proper so that a male donor may direct a urine stream onto the adsorbent. The tray is designed so that it rests in the urinal so that flushing water or chemicals do not contact the adsorbent but rather flush the surface of the urinal and the drain but not the adsorbent. This arrangement presents a number of disadvantages including the need for cooperation from the donors so that the urine passes through the adsorbent and the problems produced by the odors emanating from the unflushed filter. Cigarette butts and other debris thrown into the urinal may also contaminate or cause disassociation of the collected proteins.

British Pat. No. 1,308,727 discloses an arrangement in which an adsorbent containing filter is placed directly in the drain pipe connecting a conventional urinal to a sewer. This insures that urine voided into the urinal will pass over the adsorbent but expose the filter directly to the flow of flushing water and disinfecting chemicals placed in the urinal and makes frequent collection of the adsorbent difficult and expensive.

SUMMARY OF THE INVENTION

The present invention is broadly directed to the extraction of commercially useful biological trace compounds from human urine by the placement of a removable adsorbent filter in the flow line between the unflushed urinal and the holding tank of a portable toilet. Portable toilets of the type employed with the present invention are used at locations that don't include sufficient conventional toilets, of the type directly connected to sewer lines or waste disposal facilities, to serve the needs of local users. They are frequently used a construction sites, athletic events, concerts, and military field maneuvers and the like. They constitute a self-contained, portable, shelter including a urinal, and often a separate toilet seat. These units are connected by gravity flow lines to a holding tank disposed within the shelter which contains an odor reducing solution. Portable toilets of this type are unflushed and depend upon the odor reducing properties of the solution in the holding tank between the relatively frequent periods at which they are serviced. During this servicing, which may occur at intervals of between a few hours up to several weeks, the holding tanks are pumped out, usually into a tank truck, and are rinsed and refilled with a new supply of odor reducing solution. The urinal's collecting lines are similarly rinsed. A toilet of this broad type is disclosed in U.S. Pat. No. 3,835,480.

The present invention contemplates a portable toilet of this type having a removable adsorbent filter disposed in the gravity flow line between the urinal and the holding tank. This arrangement achieves a number of advantages. First, since the urinal is unflushed the proteins collected on the adsorbent are not disturbed. Use of the adsorbent filter does not increase the odor level in the portable toilet which the users find acceptable partly because of their infrequent use of such facilities. Secondly, removal of the absorbed filter does not require a special service call to the toilet but may be done as part of the normal process of pumping and cleaning the portable toilets. When added to the fact that the urine donors need not be paid, as they are in present commercial collection operations, the method of the present invention provides a dramatic reduction in the collection cost of the urine trace elements, relative to the previous methods.

When it is desired to collect proteins that rapidly degenerate, such as high molecular weight Urokinase, the method of the present invention may be used in connection with portable toilets employed in high usage situations such as mass attendance athletic events, so that the filters may be removed and replaced every few hours. The filter bodies can be immediately frozen, or freeze dried, to prevent any degeneration of their collected protein. The present method thus enables the collection of a higher quality urine protein at substantially lower cost than previously available methods.

Other objectives, advantages and applications of the present invention will be made apparent by the following detailed disclosure of a preferred embodiment of the invention. The description makes reference to the accompanying drawings in which:

FIG. 1 is a perspective view of a portable toilet incorporating my invention, partially broken away for purposes of illustration;

FIG. 2 is a detailed sectional view of the adsorbent filter body employed in the preferred embodiment of the invention; and FIG. 3 is a perspective view of an alternative embodiment of the invention in which the urine flows through a plurality of chambers.

The present invention utilizes a portable toilet, generally indicated at 10, to extract biological trace compounds from urine. The portable toilet includes an enclosed shelter 12, typically formed of sheet metal, plastic or wood, which may be accessed through a door 14. A holding tank 16 for excreted waste is supported within the shelter 12 near its bottom. The tank 16 may typically have a capacity of 50 gallons or so.

A toilet bowl 18, equipped with a toilet seat 20, is supported within the shelter 12 and is connected to the holding tank 16 by a gravity feed waste pipe 22. The shelter also contains a separate urinal bowl 24. The urinal 24 is typically used by males desiring to urinate and the toilet 18 is used by females for all purposes, and males for purposes of defecation.

The urinal bowl 24 is equipped with a filter drain 26 leading to a gravity feed conduit 28. The lower end of the conduit connects to the holding tank 16.

A filter chamber, generally indicated at 30, is adapted to be interconnected in the urinal flow line 28, so as to effectively divide the flow line into an upper section 28a, and a lower section 28b. The filter chamber 30 consists of a cylindrical body 32 having an open top and a bottom section leading into an outlet pipe 34. A mesh screen 36 closes off the top end of the outlet pipe 34.

The filter body is adapted to be filled with an adsorbent resin which absorbs the desired biological trace compounds and allows the main bulk of the urine, including its water content, to pass onto the holding tank 16. A variety of such adsorbent resins are well known to those skilled in the art and are commercially available in a variety of forms. The adsorbents may be of the ion exchange type or employ other well-known mechanisms. U.S. Pat. No. 3,711,377 describes a variety of adsorbents that may be employed. Other adsorbents are disclosed in U.S. Pat. No. Re. 29,980. These adsorbents are all general, collecting a variety of large molecules that may be later separated using known purification techniques.

Alternatively, a bio-specific adsorbent for the particular molecule of interest may be used. Such a bio-specific adsorbent for Urokinase is described by Maciag, T.; Weibel, M. K. and Pye, E. K. in *Methods in Enzymology*, Volume 34b, page 451 Academic Press, New York and London (1975). That adsorbent, termed BAPA-Sepharose 4B is a highly specific adsorbent for Urokinase and thus greatly simplifies the later purification process. Another general adsorbent may constitute a polystyrene non-polar adsorbent having a surface area to weight ratio of approximately 330 meters$^2$ per gram, an average pour diameter of 90 angstroms, and a skeletal density of approximately 1.07 grams per centimeter$^3$. An adsorbent which meets these specifications is Amberlite XAD-2, manufactured by Rohm and Haas Company of Philadelphia, Pennsylvania.

A suitable adsorbent 38 is packed within the cylindrical section of the filter body 32 and a cap 40 is screwed over the top of the filter body. The cap 40 contains an inlet tube 42 which slips over the downwardly depending drain tube section 28a. A filter screen 44 is fitted at the bottom of the inlet tube 42 to protect the adsorbent from gross impurities.

Urine voided into the urinal 24 then passes through the conduit section 28a, through the adsorbent, and out through the conduit section 28b and is collected in the holding tank 16. The biological trace compounds of interest are collected on the adsorbent 38.

The holding tank 16 is partially filled with a chemical solution having the capability of reducing and/or masking the odor generated by the urine and fesces deposited in the collecting tank. The holding tank may also be vented to the atmosphere in a suitable manner which is not illustrated in the drawing. As a result, the portable toilet may be used for an extended period of time, without servicing, and without generating unpleasant odors that would prevent its usage.

When the portable toilet 10 is serviced, as it must be on a regular basis, by pumping out the holding tank 16, cleaning the toilet and urinal, and replacing the odor reducing fluid within the holding tank, the filter body 30 is also removed and replaced with a fresh filter body. The saturated filter body may be immediately processed to extract the collected trace compounds or it may be shipped to a central processing site in either a frozen or an unfrozen state. Freezing slows the degradation of the large molecules of interest and also slows the putrification of other materials collected on the adsorbent which might adversely affect the trace compounds of interest.

The purification process of the resin depends upon the specific nature of the trace compounds of interest and the type of adsorbent used. The technical literature, including the previously noted patents, describe purification processes for a variety of adsorbents.

Since certain adsorbents operate best with urine of a specific pH, it is often desirable to utilize a system that compensates for the pH variations resulting from different urine donors. FIG. 3 illustrates an alternative embodiment of the invention in which two adsorbent chambers are utilized with a provision for fixing the pH of the urine prior to its entrance into the second adsorbent chamber. A urinal 202 of a suitable and aesthetically pleasing design has a center outlet 204 connected to one end of a fluid passage 206. The center outlet 204 employs a screen 208 to prevent unwanted objects from entering the fluid passage 206. A flow of urine thus passes from the urinal 202 into the fluid passage 206.

The fluid passage 206 connects to a first adsorbent chamber 210. The adsorbent chamber 210 contains an adsorbent 212 suitable to absorb desired biological compounds from the urine. The urine then flows into a fluid passage 214 to a buffer chamber 216.

The buffer chamber 216 contains a buffer such as monosodium phosphate, which fixes the pH of urine which flows through the chamber 216. Other buffers may be utilized depending upon the pH level desired. Urine then flows through a fluid passage 218 into a second adsorbent chamber 220. The chamber 220 contains an adsorbent 222 which is compatible with the adjusted pH of the urine. After passage through the chamber 220 the urine flows through a fluid passage 224 to a liquid disposal tank 226. A sewer line may be substituted for the liquid disposal tank 226 without departing from the invention. As with the first described embodiment a sterilizing agent may be utilized to prevent the growth of bacteria.

This invention has been described with reference to specific embodiments and it is to be understood that although these embodiments represent the best mode of practicing the invention known to the inventor at the time of filing the patent application, various modifications and additions to the illustrated embodiment are possible and accordingly the foregoing description is not to be construed in a limiting sense.

The embodiments of the invention in which an exclusive property or privilege is claimed are defined as follows:

1. In a flushless toilet of the type having a urinal, a holding tank containing an odor preventing chemical solution, and a gravity flow conduit connecting the urinal to the holding tank, a filter body containing an adsorbent for at least certain trace constituents of urine removably supported in the conduit intermediate the urinal and the holding tank so that urine flowing from the urinal to the holding tank contacts the adsorbent allowing urine voided into the urinal to pass through the conduit and the filter body to the holding tank under the force of gravity, the urine thereby contacting the adsorbent so that at least a portion of the trace constituents adhere to the adsorbent from which they may be extracted upon removal of the filter body from the toilet.

2. The toilet of claim 1 further including a separate toilet seat having its output connected to the holding tank.

3. The toilet of claim 1 including a unitary supporting and enclosing structure for the urinal and the holding tank, said structure including a door.

4. The toilet of claim 1 wherein the adsorbent constitutes an ion exchange resin.

5. The toilet of claim 1 further including means supported in the conduit between the urinal and the adsorbent filter for controlling the pH of urine passing through the filter.

6. A flushless portable toilet incorporating means for extracting commercially useful constituents from the urine voided into the toilet comprising: a unitary enclosed shelter having a door; a urinal supported within said shelter; a holding tank supported in said shelter at a level below the urinal, said holding tank being adapted to retain a deodorizing chemical solution for the urine; a conduit connecting the urinal to the holding tank; container means formed as part of the conduit intermediate the urinal and the holding tank for retaining a filter body; and a filter body removably disposed in the container means, the filter body constituting an adsorbent for at least certain trace constituents of urine allowing urine voided into the urinal to pass through the conduit and the filter body to the holding tank under the force of gravity, the urine thereby contacting the adsorbent so that at least a portion of the trace constituents adhere to the adsorbent from which they may be extracted upon removal of the filter body from said container means.

7. The portable toilet of claim 6 further including a toilet seat disposed within the shelter and connected to the holding tank by a gravity feed pipe.

8. The portable toilet of claim 6 further including means disposed in the conduit between the urinal and the container means for the filter body for adjusting the pH of the urine flowing through the filter body.

* * * * *